US012667271B2

(12) United States Patent
Shin et al.

(10) Patent No.: US 12,667,271 B2
(45) Date of Patent: **\*Jun. 30, 2026**

(54) SLEEP TRACKING AND VITAL SIGN MONITORING USING LOW POWER RADIO WAVES

(71) Applicant: Google LLC, Mountain View, CA (US)

(72) Inventors: Dongeek Shin, Santa Clara, CA (US); Brandon Barbello, Mountain View, CA (US); Shwetak Patel, Seattle, WA (US); Anupam Pathak, San Carlos, CA (US); Michael Dixon, Sunnyvale, CA (US)

(73) Assignee: Google LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/830,149

(22) Filed: Sep. 10, 2024

(65) Prior Publication Data

US 2025/0000380 A1      Jan. 2, 2025

Related U.S. Application Data

(63) Continuation of application No. 17/608,319, filed as application No. PCT/US2019/031290 on May 8, 2019, now Pat. No. 12,127,825.

(51) Int. Cl.
*A61B 5/0507* (2021.01)
*A61B 5/00* (2006.01)
(Continued)

(52) U.S. Cl.
CPC ............ *A61B 5/0507* (2013.01); *A61B 5/024* (2013.01); *A61B 5/0816* (2013.01);
(Continued)

(58) Field of Classification Search
CPC ..... A61B 5/0507; A61B 5/024; A61B 5/0816; A61B 5/1116; A61B 5/4815;
(Continued)

(56) References Cited

U.S. PATENT DOCUMENTS 6,234,982 B1      5/2001  Aruin
7,956,755 B2      6/2011  Lee et al.
(Continued)

FOREIGN PATENT DOCUMENTS

CN          108700645 A      10/2018
CN          108877126 A      11/2018
(Continued)

*Primary Examiner* — Adil Partap S Virk
(74) *Attorney, Agent, or Firm* — Lerner David LLP

(57)                ABSTRACT

Various arrangements for performing radar-based measurement of vital signs. Waveform data may be received then filtered of data indicative of static objects to obtain motion-indicative waveform data. The motion-indicative waveform data may be analyzed to determine one or more frequencies of movement present within the motion-indicative waveform data. A spectral analysis may be performed on the motion-indicative waveform data to determine a spectral-analysis state of a monitored region. The spectral-analysis state of the monitored region may be determined to match a predefined spectral-analysis state during which vital sign monitoring is permitted. One or more vital signs of a monitored user present within the monitored region may be determined and output based on analyzing the motion-indicative waveform data.

20 Claims, 8 Drawing Sheets

(51) Int. Cl.

| | |
|---|---|
| *A61B 5/024* | (2006.01) |
| *A61B 5/08* | (2006.01) |
| *A61B 5/11* | (2006.01) |
| *G01S 13/28* | (2006.01) |

(52) U.S. Cl.
CPC .......... *A61B 5/1116* (2013.01); *A61B 5/4815* (2013.01); *A61B 5/6898* (2013.01); *A61B 5/725* (2013.01); *A61B 5/7267* (2013.01); *G01S 13/282* (2013.01)

(58) Field of Classification Search
CPC ..... A61B 5/6898; A61B 5/725; A61B 5/7267; A61B 5/1115; A61B 5/1118; A61B 5/7207; A61B 5/7221; A61B 5/7264; G01S 13/282
See application file for complete search history.

(56) References Cited

U.S. PATENT DOCUMENTS

| | | | |
|---|---|---|---|
| 8,063,764 | B1 | 11/2011 | Mihailidis et al. |
| 8,740,793 | B2 | 6/2014 | Cuddihy et al. |
| 10,055,961 | B1 | 8/2018 | Johnson et al. |
| 10,172,592 | B2 * | 1/2019 | Ward, III ............. A61B 8/5223 |
| 10,310,073 | B1 * | 6/2019 | Santra ................... A61B 5/0816 |
| 10,412,206 | B1 * | 9/2019 | Liang ................. H04M 3/42068 |
| 10,568,565 | B1 * | 2/2020 | Kahn .................... A61B 5/1126 |
| 10,617,330 | B1 * | 4/2020 | Joshi ....................... G06V 20/10 |
| 10,702,207 | B2 * | 7/2020 | Long .................... A61B 5/7257 |
| 10,901,069 | B2 | 1/2021 | Otsuki et al. |
| 10,945,659 | B1 * | 3/2021 | Kahn .................... A61B 5/4812 |
| 11,012,285 | B2 * | 5/2021 | Chen .................... H04W 72/21 |
| 11,074,800 | B2 | 7/2021 | Li et al. |
| 11,250,683 | B2 | 2/2022 | Sundholm |
| 11,257,346 | B1 | 2/2022 | Meyers et al. |
| 11,311,202 | B2 * | 4/2022 | Bliss .................. A61B 5/02444 |
| 11,406,281 | B2 | 8/2022 | Shin et al. |
| 11,426,120 | B2 | 8/2022 | Cho et al. |
| 11,627,890 | B2 | 4/2023 | Shin et al. |
| 11,754,676 | B2 | 9/2023 | Shin et al. |
| 11,808,839 | B2 | 11/2023 | Shin et al. |
| 11,832,961 | B2 | 12/2023 | Shin et al. |
| 11,857,331 | B1 | 1/2024 | Berme et al. |
| 11,875,659 | B2 | 1/2024 | Shin et al. |
| 11,967,217 | B1 | 4/2024 | Andrews et al. |
| 12,127,825 | B2 * | 10/2024 | Shin ..................... A61B 5/4815 |
| 2001/0004234 | A1 | 6/2001 | Petelenz et al. |
| 2002/0116080 | A1 | 8/2002 | Birnbach et al. |
| 2003/0001791 | A1 | 1/2003 | Barquist et al. |
| 2003/0058111 | A1 | 3/2003 | Lee et al. |
| 2003/0058341 | A1 | 3/2003 | Brodsky et al. |
| 2006/0001545 | A1 | 1/2006 | Wolf |
| 2007/0100666 | A1 | 5/2007 | Stivoric et al. |
| 2008/0004904 | A1 | 1/2008 | Tran |
| 2008/0252445 | A1 | 10/2008 | Kolen |
| 2010/0102971 | A1 * | 4/2010 | Virtanen .................. A61B 5/11 381/122 |
| 2012/0092284 | A1 | 4/2012 | Rofougaran et al. |
| 2012/0101411 | A1 | 4/2012 | Hausdorff et al. |
| 2012/0101770 | A1 | 4/2012 | Grabiner et al. |
| 2013/0002434 | A1 | 1/2013 | Cuddihy et al. |
| 2013/0030257 | A1 | 1/2013 | Nakata et al. |
| 2013/0053653 | A1 | 2/2013 | Cuddihy et al. |
| 2013/0072807 | A1 | 3/2013 | Tran |
| 2013/0100268 | A1 | 4/2013 | Mihailidis et al. |
| 2013/0143519 | A1 | 6/2013 | Doezema |
| 2013/0172691 | A1 | 7/2013 | Tran |
| 2013/0278465 | A1 | 10/2013 | Owen |
| 2013/0303860 | A1 | 11/2013 | Bender et al. |
| 2014/0024917 | A1 * | 1/2014 | McMahon ........... A61B 5/1126 600/407 |
| 2014/0062702 | A1 | 3/2014 | Ardres et al. |
| 2014/0266787 | A1 | 9/2014 | Tran |
| 2014/0340227 | A1 | 11/2014 | Reed, Jr. |

| | | | |
|---|---|---|---|
| 2015/0099941 | A1 | 4/2015 | Tran |
| 2015/0125832 | A1 | 5/2015 | Tran |
| 2015/0219755 | A1 * | 8/2015 | Borggaard ................ G01S 5/30 367/118 |
| 2015/0301615 | A1 * | 10/2015 | Kasar ....................... G06F 3/017 345/156 |
| 2016/0137258 | A1 | 5/2016 | Alvarez-icaza et al. |
| 2016/0328941 | A1 | 11/2016 | Sundholm |
| 2017/0181691 | A1 * | 6/2017 | Olivier ................. A61B 5/1102 |
| 2017/0221335 | A1 | 8/2017 | Brillaud |
| 2017/0270481 | A1 | 9/2017 | Morgenthau et al. |
| 2017/0273635 | A1 | 9/2017 | Li et al. |
| 2017/0352240 | A1 | 12/2017 | Carlton-foss |
| 2018/0008169 | A1 | 1/2018 | Chang |
| 2018/0049669 | A1 * | 2/2018 | Vu ........................ A61B 5/0507 |
| 2018/0103874 | A1 | 4/2018 | Lee et al. |
| 2018/0121861 | A1 | 5/2018 | Morgenthau et al. |
| 2018/0151037 | A1 | 5/2018 | Morgenthau et al. |
| 2018/0235518 | A1 | 8/2018 | Barton |
| 2018/0292523 | A1 | 10/2018 | Orenstein et al. |
| 2018/0367952 | A1 | 12/2018 | Devdas et al. |
| 2019/0044485 | A1 | 2/2019 | Rao et al. |
| 2019/0099113 | A1 | 4/2019 | Roder et al. |
| 2019/0108742 | A1 | 4/2019 | Stolbikov et al. |
| 2019/0117125 | A1 | 4/2019 | Zhang et al. |
| 2019/0130725 | A1 | 5/2019 | Dempsey |
| 2019/0348209 | A1 * | 11/2019 | Wen ......................... H04B 5/26 |
| 2020/0026361 | A1 | 1/2020 | Baheti et al. |
| 2020/0034739 | A1 | 1/2020 | Chung et al. |
| 2020/0090484 | A1 | 3/2020 | Chen et al. |
| 2020/0118410 | A1 | 4/2020 | Lindstrom et al. |
| 2020/0146550 | A1 | 5/2020 | Tunnell et al. |
| 2020/0166611 | A1 | 5/2020 | Lin et al. |
| 2020/0170514 | A1 * | 6/2020 | Hui ...................... A61B 5/1126 |
| 2020/0178892 | A1 * | 6/2020 | Maslik ................. A61B 5/4836 |
| 2020/0191913 | A1 * | 6/2020 | Zhang .................... G01S 7/412 |
| 2020/0234030 | A1 | 7/2020 | Baheti et al. |
| 2020/0237252 | A1 | 7/2020 | Lane et al. |
| 2020/0284901 | A1 | 9/2020 | Tierney et al. |
| 2020/0289033 | A1 | 9/2020 | Sivertsen et al. |
| 2020/0367810 | A1 * | 11/2020 | Shouldice ............ A61B 5/4818 |
| 2020/0408879 | A1 * | 12/2020 | Mayer ................... G01S 13/583 |
| 2021/0142643 | A1 | 5/2021 | Susna et al. |
| 2021/0142894 | A1 * | 5/2021 | Räisänen ................. A61B 5/00 |
| 2021/0197834 | A1 | 7/2021 | Shaker et al. |
| 2021/0217288 | A1 | 7/2021 | Sundholm |
| 2021/0256829 | A1 | 8/2021 | Ten Kate et al. |
| 2021/0264762 | A1 | 8/2021 | Lunner et al. |
| 2021/0275056 | A1 | 9/2021 | Mcmahon et al. |
| 2021/0298643 | A1 | 9/2021 | Baker et al. |
| 2021/0322856 | A1 | 10/2021 | Virkar et al. |
| 2022/0007965 | A1 * | 1/2022 | Tiron ................... A61B 5/0823 |
| 2022/0007970 | A1 | 1/2022 | Almeida |
| 2022/0058971 | A1 * | 2/2022 | Mankodi ............. A61B 5/7455 |
| 2022/0268916 | A1 | 8/2022 | Nagpal |
| 2022/0361810 | A1 | 11/2022 | Price |
| 2023/0000377 | A1 * | 1/2023 | Wu ........................ G06V 40/15 |
| 2023/0037749 | A1 | 2/2023 | Kadam et al. |
| 2023/0419672 | A1 | 12/2023 | Prendergast et al. |
| 2024/0115202 | A1 | 4/2024 | Tran |

FOREIGN PATENT DOCUMENTS

| | | |
|---|---|---|
| CN | 111481184 A | 8/2020 |
| DE | 102018105875 A1 | 9/2019 |
| EP | 4203782 B1 | 6/2024 |
| JP | 2009528859 A | 8/2009 |
| JP | 2014039586 A | 3/2014 |
| JP | 2014516681 A | 7/2014 |
| JP | 2016005596 A | 1/2016 |
| JP | 2017181225 A | 10/2017 |
| JP | 2019023595 A | 2/2019 |
| JP | 2020056629 A | 4/2020 |
| KR | 20190104484 A | 9/2019 |
| KR | 20200103749 A | 9/2020 |
| WO | 2013/040511 A1 | 3/2013 |
| WO | 2016021236 A1 | 2/2016 |

(56) References Cited

FOREIGN PATENT DOCUMENTS

| WO | 2019005936 | A1 | 1/2019 |
| --- | --- | --- | --- |
| WO | 2019242904 | A1 | 12/2019 |
| WO | 2020012455 | A1 | 1/2020 |

* cited by examiner

600

SLEEP TRACKING AND VITAL SIGN MONITORING USING LOW POWER RADIO WAVES

CROSS-REFERENCE TO RELATED APPLICATIONS

This application is a continuation of U.S. application Ser. No. 17/608,319, filed Nov. 2, 2021, and titled "SLEEP TRACKING AND VITAL SIGN MONITORING USING LOW POWER RADIO WAVES," which is a 371 National Stage filing of PCT Application No. PCT/US2019/031290, filed May 8, 2019, and titled "SLEEP TRACKING AND VITAL SIGN MONITORING USING LOW POWER RADIO WAVES," which are hereby incorporated by reference in their entirety for all purposes.

BACKGROUND

Vital signs, such as heartrate and breathing rate, can be useful for monitoring a person's health. Additionally, the amount a person moves while sleeping can be indicative of how soundly he is sleeping and of other health characteristics. Typically, to capture vital signs, perform sleep tracking, or both a sensor needs to be placed directly on the skin of the user being monitored. Such an arrangement, especially while sleeping, may not be desirable. Wearing such a sensor can be uncomfortable or easily forgotten by the user before going to bed. Further, such a contact sensor can become displaced during sleeping and may stop accurately sensing the user's vital signs and/or sleep patterns, resulting in a loss of valuable data.

SUMMARY

Various embodiments are described related to a smart-home device that performs radar-based measurement of vital signs. In some embodiments, a smart-home device that performs radar-based measurement of vital signs is described. The device may include a housing. The device may include an RF emitter located within the housing. The device may include an RF receiver located within the housing. The device may include a radar processing circuit located within the housing that may process data received from the RF receiver and may output raw waveform data to a processing system. The device may include a processing system, comprising one or more processors, that may be in communication with the radar processing circuit. The processing system may be configured to receive the raw waveform data from the radar processing circuit. The processing system may be configured to filter, from the waveform data, waveform data indicative of static objects to obtain motion-indicative waveform data. The processing system may be configured to analyze the motion-indicative waveform data to determine one or more frequencies of movement present within the motion-indicative waveform data. The processing system may be configured to perform spectral analysis on the motion-indicative waveform data to determine a spectral-analysis state of a monitored region. The processing system may be configured to determine that the spectral-analysis state of the monitored region matches a predefined spectral-analysis state during which vital sign monitoring may be permitted. The processing system may be configured to, in response to determining that the spectral-analysis state of the monitored region matches the spectral-analysis state during which vital sign monitoring may be permitted, determine one or more vital signs of a monitored user present within the monitored region based on analyzing the motion-indicative waveform data. The processing system may be configured to output the one or more determined vital signs of the monitored user.

Embodiments of such a method may include one or more of the following features: The RF emitter may emit frequency-modulated continuous-wave (FMCW) radar. The processing system may be further configured to filter the one or more frequencies to sum harmonics of the one or more frequencies caused by the one or more vital signs. The processing system being configured to determine that the spectral-analysis state of the monitored region matches the spectral-analysis state during which vital sign monitoring may be permitted comprises the processing system being further configured to use a neural network to analyze the spectral-analysis state of the monitored region. The smart-home device may be a smartphone. The device may further include a smartphone charger stand. The smartphone may be docked with the smartphone charger stand such that a radar sensor of the smartphone may be pointed to emit radio waves at a location where the monitored user will be sleeping. The smartphone may be placed under a sleeping location such that a radar sensor of the smartphone may be pointed to emit radio waves at the sleeping location where the monitored user will be sleeping. The one or more vital signs may include a breathing rate. The one or more vital signs may include a heartrate.

In some embodiments, a method for radar-based measurement of vital signs is described. The method may include receiving, by a smart-home device, waveform data based on received radio waves. The method may include filtering, from the waveform data, waveform data indicative of static objects to obtain motion-indicative waveform data. The method may include analyzing the motion-indicative waveform data to determine one or more frequencies of movement present within the motion-indicative waveform data. The method may include performing spectral analysis on the motion-indicative waveform data to determine a spectral-analysis state of a monitored region. The method may include determining that the spectral-analysis state of the monitored region matches a predefined spectral-analysis state during which vital sign monitoring may be permitted. The method may include determining one or more vital signs of a monitored user present within the monitored region based on analyzing the motion-indicative waveform data. The method may include, in response to determining that the spectral-analysis state of the monitored region matches the spectral-analysis state during which vital sign monitoring is permitted, recording the one or more determined vital signs of the monitored user.

Embodiments of such a method may include one or more of the following features: The emitted radio waves may be emitted as part of frequency-modulated continuous-wave (FMCW) radar. The method may include filtering the one or more frequencies to sum harmonics of the one or more frequencies caused by the one or more vital signs to one or more fundamental frequencies of the one or more vital signs. Determining that the spectral-analysis state of the monitored region matches the spectral-analysis state during which vital sign monitoring may be permitted comprises using a neural network to analyze the spectral-analysis state of the monitored region. The method may further include emitting, by the smart-home device, radio waves at a monitored region. The smart-home device may be a smartphone. The method may include docking the smartphone with a charger stand such that a radar sensor of the smartphone may be pointed to emit radio waves at a location where the monitored user will be sleeping. The method may include placing the smartphone under a sleeping location such that a radar sensor of the smartphone may be pointed to emit radio waves at the sleeping location where the monitored user will be sleeping. The one or more vital signs may include a breathing rate. The one or more vital signs may include a heartrate.

In some embodiments, a non-transitory processor-readable medium comprising processor-readable instructions is described. The processor-readable instructions may be configured to cause the one or more processors to receive raw waveform data. The one or more processors may filter, from the waveform data, waveform data indicative of static objects to obtain motion-indicative waveform data. The one or more processors may analyze the motion-indicative waveform data to determine one or more frequencies of movement present within the motion-indicative waveform data. The one or more processors may perform spectral analysis on the motion-indicative waveform data to determine a spectral-analysis state of a monitored region. The one or more processors may determine that the spectral-analysis state of the monitored region matches a predefined spectral-analysis state during which vital sign monitoring may be permitted. The one or more processors may determine one or more vital signs of a monitored user present within the monitored region based on analyzing the motion-indicative waveform data. In response to determining that the spectral-analysis state of the monitored region matches the spectral-analysis state during which vital sign monitoring is permitted, the one or more processors may output the one or more determined vital signs of the monitored user.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

A smart home device, such as a smartphone, tablet computer, home assistant device, may have integrated low-power radar circuitry or be connected with an external radar device. Such low power radar circuitry may have many uses. Possible uses can include measuring vital signs of a user, tracking sleep patterns of the user, or both. Traditionally, to measure vital signs of a user, a sensor needs to be in contact with the user's skin, such as a chest-band or wrist-band. However, by using radar, it can be possible to identify large movements of the user that are indicative of sleep patterns and, in some circumstances, small movements of the user that are attributed to vital signs, such as the user's breathing and the user's heartrate.

Such a radar-based arrangement that does not require any sensor to be in physical contact with the user being monitored may be especially beneficial since a smart home device may be temporarily placed (e.g., in the case of a smartphone), semi-permanently installed (e.g., in the case of a home assistant device), or permanently installed bedside. For example, when a user goes to bed, she may already be in the habit of leaving the smartphone charging on a stand or connected with a wired charger wire nearby. Thus with little to no adjustment of the user's routine, the user may be able to reliably gather vital signs and sleep tracking data while the user is sleeping.

A smart home device may emit radar, such as frequency-modulated continuous-wave (FMCW) radar. Such radio waves may be transmitted at or around 60 GHz. Reflected radar pulses may be used to determine both distance and phase shifts. By comparing raw waveform data from multiple reflected radar pulses, reflected waveform data corresponding to static objects may be identified. Waveform data corresponding to static objects may be filtered out such that motion-indicative waveform data is obtained. The motion indicative waveform data may then be analyzed to identify one or more frequencies corresponding to vital signs. The motion indicative waveform data may be further processed using machine-learning, such as a neural network, to classify whether the user was generally still or moving when the motion indicative waveform data was captured. This data may be used to perform sleep tracking and determine whether vital signs, such as heartrate and breathing rate, were gathered while the monitored user was generally still.

Figure 1A:
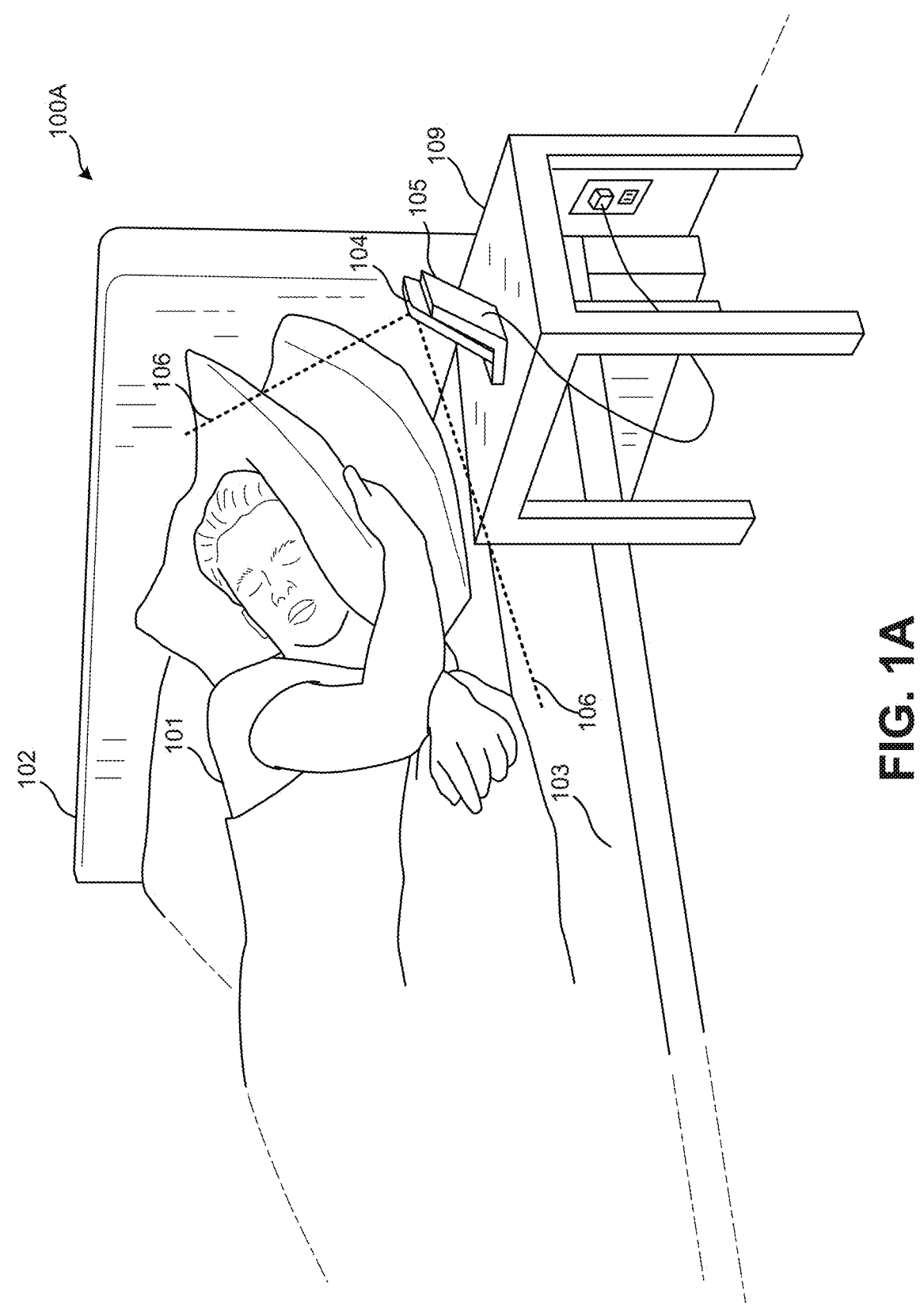
FIG. 1A illustrate an embodiment of a bedside smart home device using low power radio waves to perform sleep tracking and vital sign monitoring.

FIG. 1A illustrate an embodiment 100A of a bedside smart home device using low power radio waves to perform sleep tracking and vital sign monitoring. In embodiment 100A, user 101 is being monitored while sleeping. User 101 has placed his smartphone 104, which is functioning as a smart home device, on wireless charging cradle 105 on nightstand 109. Smartphone 104 may be generally placed on a horizontal plane with the sleeping user and has its radar emitter and receiver pointed towards user 101. Radio waves may be emitted and sensed in field 106. User 101 is the closest person to smartphone 104. Static objects that are not expected to move may be in the region monitored by smartphone 104. For example, static objects in the monitored region can include headboard 102, mattress 103, and/or nightstand 109 (or some other form of table or flat surface that wireless charging cradle 105 can be placed on. These objects may reflect a significant amount of emitted radio waves, but, as detailed herein, movement data due to vitals of user 101 can successfully be filtered out.

5

Figure 1B:
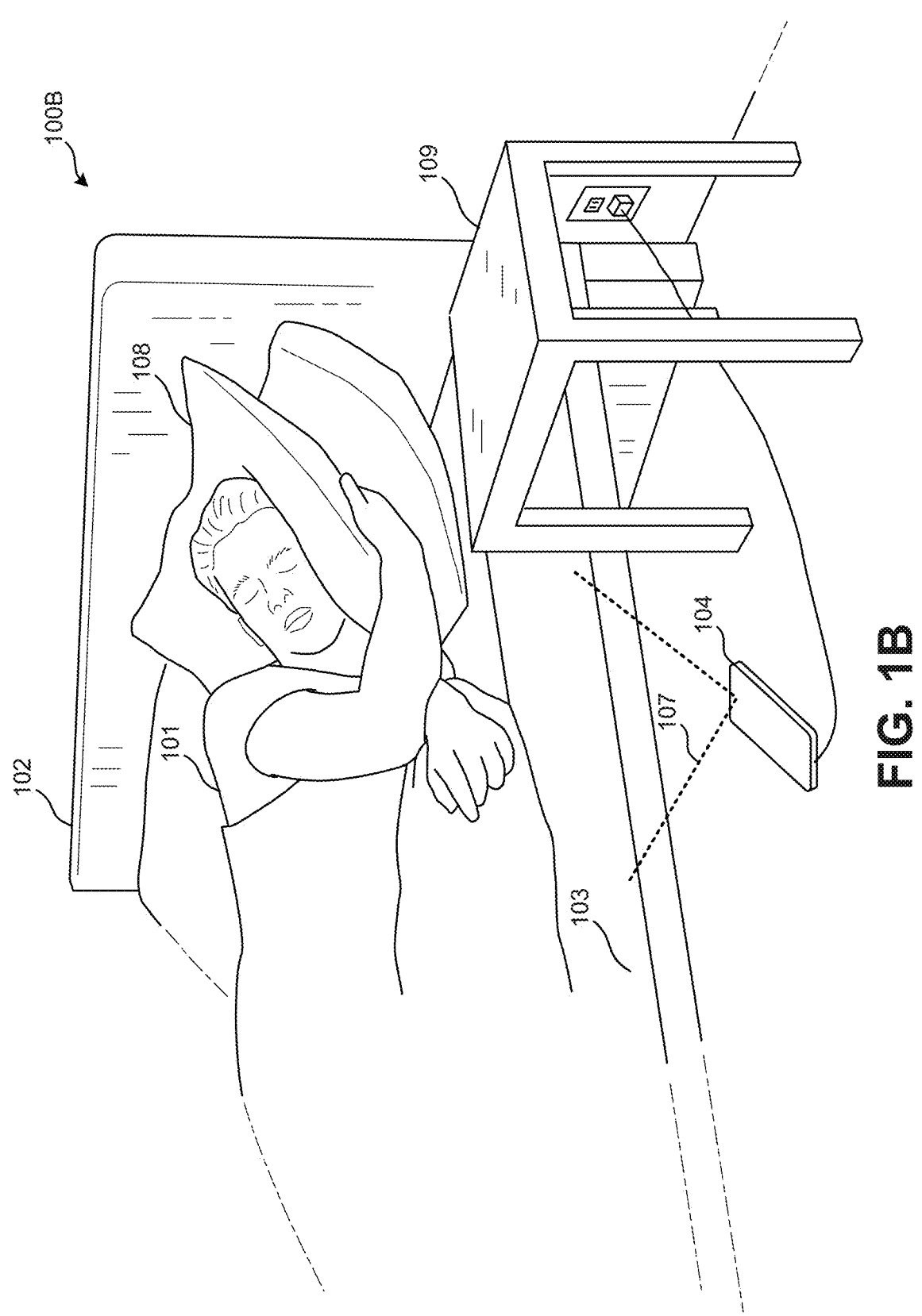
FIG. 1B illustrate an embodiment of an under-bed smart home device using low power radio waves to perform sleep tracking and vital sign monitoring.

FIG. 1B illustrate an embodiment 100B of an under-bed smart home device using low power radio waves to perform sleep tracking and vital sign monitoring. Such an arrangement may be beneficial if user 101 does not have access to a stand that can effectively point smartphone 104 at user 101 from nightstand 109. In embodiment 100B, user 101 is being monitored while sleeping. User 101 has placed his smartphone 104, which is functioning as a smart home device, under his bed. Smartphone 104 may be generally placed such that its RF emitter and RF receiver are pointed towards user 101 from under mattress 103. (If a box spring is located between smartphone 104 and user 101, while metal may tend to interfere with the emitted radio waves, the metal of the box spring may typically be sparse enough to allow monitoring of user 101.) Radio waves may be emitted and sensed in field 107. The frequency of wavelength emitted may penetrate through the bedframe, mattress, and bedding such that vitals and movement of user 101 can be monitored. User 101 is the closest person to smartphone 104. Static objects that are not expected to move may be in the region monitored by smartphone 104. Similar to embodiment 100A, static objects in the monitored region can include headboard 102 and mattress 103. In other embodiments, smartphone 104 may be placed between pillow 108 and mattress 103.

Figure 2:
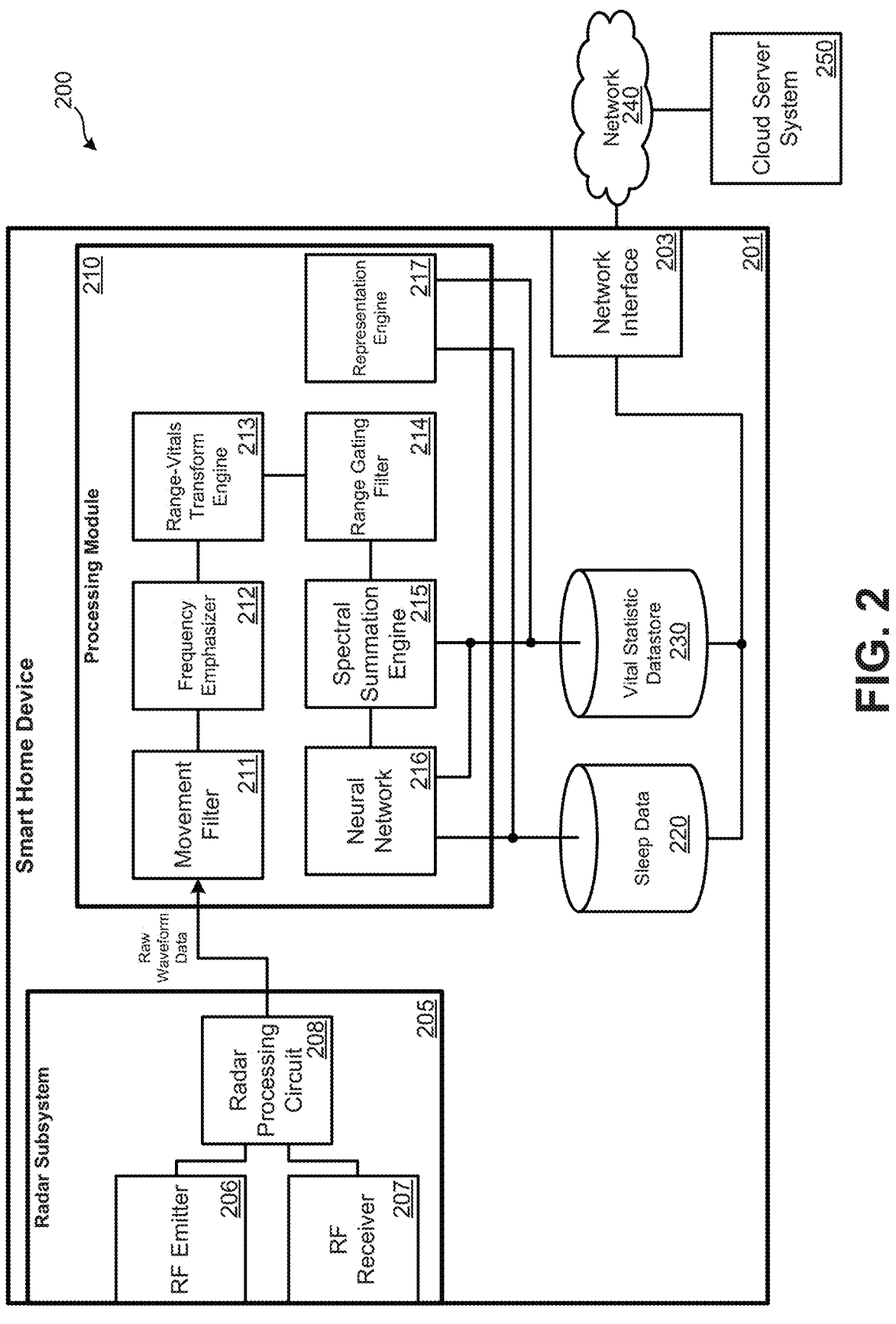
FIG. 2 illustrates an embodiment of a sleep tracking and vital sign monitoring system.

FIG. 2 illustrates an embodiment of a sleep tracking and vital sign monitoring system 200. System 200 may include smart home device 201, network 240, and cloud server system 250. Smart home device 201 can represent various computerized devices that may be found within a home, such as in a region where a user may sleep. For example, smart home device 201 may be a cellular phone or smartphone. Smart home device 201 may be a home assistant device, such as a Google® Home or Amazon® Alexa. Such a home assistant device may be interacted with via voice commands spoken by a user. The home assistant device may then respond to the user's command via synthesized speech, for example: "Hi Computer, please enable sleep and vital tracking." Other possible forms of smart home device 201 can include: smart earbuds, a smart thermostat; a smart smoke and/or carbon monoxide detector; a smart doorbell; a smart watch; a robotic device; or a smart security camera.

Smart home device 201 may include network interface 203, radar subsystem 205, processing module 210, sleep data datastore 220; and vital statistic datastore 230. Radar subsystem 205 may include RF emitter 206, RF receiver 207, and radar processing circuit 208. RF emitter 206 can emit radio waves, such as in the form of continuous-wave (CW) radar. RF emitter 206 may use frequency-modulated continuous-wave (FMCW) radar. The FMCW radar may operate in a continuous sparse-sampling mode over a relatively long period of time. RF emitter 206 may transmit at or about 60 GHz. The power level used for transmission may be very low such that radar subsystem only has an effective range of several meters or even a shorter distance. RF receiver 207 may receive radio wave reflections off of nearby objects of radio waves emitted by RF emitter 206. The reflected radio waves may be interpreted by radar processing circuit 208. Radar processing circuit 208 may output raw waveform data, which can also be referred to as the raw "waterfall" data for analysis by a separate processing entity. Radar subsystem 205 may be incorporated together as part of a single integrated circuit (IC) or radar processing circuit 208 may be a single IC that is in communication with RF emitter 206 and RF receiver 207. In some embodiments, radar subsystem is integrated as part of smart home device 201. For instance, a smartphone may have a RF emitter 206 and RF receiver 207 arranged such that radio waves are emitted in the same direction in which a screen of the smartphone is facing. In other embodiments, an external device that includes radar subsystem 205 may be connected with smart home device 201 via wired or wireless communication. For example, radar subsystem 205 may be an add-on device to a home assistant or may be incorporated as part of a charging stand for a smartphone.

For radar subsystem 205, if FMCW is used, an unambiguous FMCW range may need to be defined. Within this range, objects can be accurately determined to be nearer or farther away. However, outside of this range, if an object is detected, it could incorrectly interpreted as nearer than an object within the unambiguous range. When using smart home device 201 to monitor sleep patterns and vital statistics, a user may be instructed that the user should be the closest person to the smart home device 201. However, it may be possible that another person or an animal is present within the bed. It may be necessary to the define the FMCW unambiguous range to be far enough, such as two meters, such that both persons (or, approximately the width of the bed) falls within the unambiguous FMCW range of radar subsystem 205. Two meters may an ideal distance since it is approximately the width of a large commercially-available bed (e.g., a king size bed).

Raw waveform data may be passed from radar subsystem 205 to processing module 210. Processing module 210 may include one or more processors. Processing module 210 may include one or more special-purpose or general-purpose processors. Special-purpose processors may include processors that are specifically designed to perform the functions detailed herein. Such special-purpose processors may be ASICs or FPGAs which are general-purpose components that are physically and electrically configured to perform the functions detailed herein. General-purpose processors may execute special-purpose software that is stored using one or more non-transitory processor-readable mediums, such as random access memory (RAM), flash memory, a hard disk drive (HDD), or a solid state drive (SSD). Processing module 210 may include: movement filter 211; frequency emphasizer 212; range-vitals transform engine 213; range gating filter 214; spectral summation engine 215; and neural network 216. Each of the components of processing module 210 may be implemented using software or as specialized hardware.

The raw waveform data output by radar subsystem 205 may be received by processing module 210 and first processed using movement filter 211. In some embodiments, it is important that movement filter 211 is initially used to perform filtering. That is, the processing performed by processing module 210 may not be commutative. Typically, vital sign determination and sleep monitoring may occur when a monitored user is sleeping or attempting to sleep in a bed. In such an environment, there may typically be little movement. Such movement may be attributed to the user moving within the bed (e.g., rolling over while trying to get to sleep or while asleep) and the user's vital signs, including movement due to breathing and movement due to the monitored user's heartbeat. In such an environment, a large portion of emitted radio waves from RF emitter 206 may be reflected by static objects in the vicinity of the monitored user, such as a mattress, box spring, bed frame, walls, furniture, bedding, etc. Therefore, a large portion of the raw waveform data received from radar subsystem 205 may be unrelated to user movements and the user's vital measurements.

Movement filter 211 may include a waveform buffer that buffers receive "chirps" or slices of received raw waveform data. For instance, sampling may occur at a rate of 10 Hz. In other embodiments sampling may be slower or faster. Movement filter 211 may buffer twenty seconds of received raw waveform chirps. In other embodiments, a shorter or longer duration of buffered raw waveform data is stored. This buffered raw waveform data can be filtered to remove raw waveform data indicative of stationary objects. That is, for objects that are moving, such as a monitored user's chest, the user's heartbeat and breathing rate will affect the distance and velocity measurements made by radar subsystem 205 and output to movement filter 211. This movement of the user will result in "jitter" in the received raw waveform data over the buffered time period. More specifically, jitter refers to the phase shifts caused by moving objects reflecting emitted radio waves. Rather than using the reflected FMCW radio waves to determine a velocity of the moving objects, the phase shift induced by the motion in the reflected radio waves is used to measure vital statistics, including heartrate and breathing rate, as detailed herein.

For stationary objects, such as furniture, a zero phase shift (i.e., no jitter) will be present in the raw waveform data over the buffered time period. Movement filter 211 can subtract out such raw waveform data corresponding to stationary objects such that motion-indicative raw waveform data is passed to frequency emphasizer 212 for further analysis. Raw waveform data corresponding to stationary objects may be discarded or otherwise ignored for the remainder of processing. by processing module 210.

In some embodiments, an infinite impulse response (IIR) filter is incorporated as part of movement filter 211. Specifically, a single-pole IIR filter may be implemented to filter out raw waveform data that is not indicative of movement. Therefore, the single-pole IIR filter may be implemented as a high-pass, low-block filter that prevents raw waveform data indicative of movement below a particular frequency from passing through to frequency emphasizer 212. The cut-off frequency may be set based on known limits to human vital signs. For example, a breathing rate may be expected to be between 10 and 60 breaths per minute. Movement data indicative of a low frequency than 10 breaths per minute may be excluded by the filter. In some embodiments, a band-pass filter may be implemented to exclude raw waveform data indicative of movement at high frequencies that are impossible or improbable for human vital signs. For instance, a heartrate, which can be expected to be above a breathing rate, may be unlikely to be above 150 beats per minute. Raw waveform data indicative of a higher frequency may be filtered out by the band pass filter.

In some embodiments, it may be possible to further fine-tune the frequencies of raw waveform data that movement filter 211 passes to frequency emphasizer 212. For instance during an initial configuration phase, a user may provide information about the monitored user (e.g., himself, a child), such as age data. Table 1 indicates typical respiratory rates for various ages. Similar data may be present for heartrate. The filter may be configured to exclude data that is outside of the expected breathing rate, heartrate range, or both.

TABLE 1

| Age | Breathing Rate Range (breaths per minute) |
|---|---|
| Birth-6 weeks | 30-60 |
| 6 months | 25-40 |
| 3 years | 20-30 |
| 6 years | 18-25 |
| 10 years | 17-23 |

TABLE 1-continued

| Age | Breathing Rate Range (breaths per minute) |
|---|---|
| Adults | 12-18 |
| 65-80 years old | 12-28 |
| >80 years old | 10-30 |

The vital signs of the monitored user being measured are periodic impulse event: a user's heartrate may vary overtime, but it can be expected that the user's heart will continue to beat periodically. This beating is not a sinusoidal function, but rather can be understood as an impulse event, more analogous to a square wave having a low duty cycle that induces motion in the user's body. Similarly, a user's breathing rate may vary over time, but breathing is a periodic function performed by the user's body that is analogous to sinusoidal function, except that a user's exhale is typically longer than an his inhale. Further, at any given time, only a particular window of waveform data is being analyzed. Since only a particular window of waveform data is being analyzed, even a perfect sinusoid within that window can result in spectral leakage in the frequency domain. Frequency components due to this spectral leakage should be deemphasized.

Frequency emphasizer 212 may work in conjunction with range-vitals transform engine 213 to determine the one (e.g., breathing) or two (e.g., breathing plus heartbeat) frequency components of the raw waveform data. Frequency emphasizer 212 may use windowing, such as a 2D Hamming window (other forms of windowing is possible, such as a Hann window), to emphasize important frequency components of the raw waveform data and to deemphasize or remove waveform data that is attributable to spectral leakage outside of the defined window. Such windowing may decrease the magnitude of raw waveform data that is likely due to processing artifacts. The use of windowing can help reduce the effects of data-dependent processing artifacts while preserving data relevant for being able to separately determine heartrate and breathing rate.

Since heartrate and breathing rate are periodic impulse events, in the frequency domain heartrate and breathing rate may be represented by different fundamental frequency, but each may have many harmonic components at higher frequencies. One of the primary purposes of frequency emphasizer 212 is to prevent the frequency ripples of harmonics of the monitored user's breathing rate from affecting the frequency measurement of the monitored user's heartrate (or the reverse). While frequency emphasizer 212 may use a 2D Hamming window, it should be understood that other windowing functions or isolating functions can be used to help isolate frequency ripples of the monitored user's breathing rate from the frequency ripples of the monitored user's heartrate.

Range-vitals transform engine 213 analyzes the received motion-filtered waveform data to identify and quantify the magnitude of movement at specific frequencies. The analysis of range-vitals transform engine 213 may assume that the frequency components of the motion waveform data is sinusoidal. Further, the transform used at by range-vitals transform engine 213 can also identify the distance at which the frequency is observed. Frequency, magnitude, and distance can all be determined at least in part because radar subsystem uses FMCW radar system.

Prior to applying the transform of range-vitals transform engine 213, a zero-padding process may be performed by range-vitals transform engine 213 to add a number of zeros to the motion-filtered raw waveform data. By performing a zero-padding process, the resolution within the frequency domain can be increased effectively allowing for more accurate low-rate measurements (e.g., a low heartrate, a low breathing rate). For example, zero-padding can help artificially increase resolution to detect differences of half a breath per minute compared to a resolution of a breath per minute without zero-padding. In some embodiments, three to four times the number of zeros compared to the buffered sample size of the raw waveform data may be added. For example, if twenty seconds of buffered raw waveform data is analyzed, sixty to eighty seconds of zero padding may be added to the sample. Specifically, the range of three to four times zero padding of the sample was found to substantially increase resolution while not making the transform process overly complex (and, thus, processor use intensive).

In order to determine the amount of zero padding to be performed, equations 1-3 may be used. In equation 1, RPM_resolution may ideally be less than 1.

$$RPM_{resolution} = 60 * \frac{chirp\_rate}{n\_fft\_slow\_time} \qquad \text{Eq. 1}$$

$$n\_FFT\_slow\_time\_min = (nearest\_power\_of\_2)(60 * chirp\_rate) \qquad \text{Eq. 2}$$

In some embodiments, a chirp rate (chirp_rate) of 30 Hz may be used. Such a frequency may have sufficient margin from Nyquist limits of the upper limit of breathing rate and heartbeat rate. n_FFT_slow_time_min may, therefore, be 2048. Given a 20 second window for estimating respiration statistics, Equation 3 results in a value of 600.

$$n\_chirps\_for\_respiration = 20 * chirp\_rate = 600 \qquad \text{Eq. 3}$$

This value of 600 is smaller than the required vitals-FFT size and makes us to perform a 3× to 4× zero padding. A balance in how much zero padding to perform may be based on increasing the frequency resolution and associated increases in the amount of computation needed to perform the FFT. A 3× to 4× zero padding has been found to provide sufficient resolution for heartrate and breath rate while moderating the amount of computation needing to be performed.

Range-vitals transform engine 213 can perform a Fourier transform (FT) to determine the frequency components of the received raw waveform data. Specifically, a fast Fourier transform (FFT) may be performed by range-vital transform engine 213 to determine the specific frequencies and magnitudes of waveform data at such frequencies. Following range-vitals transform engine 213 identifying the frequency, magnitude, and distance determination, further analysis may be needed to further reduce the effects of heartrate, breathing rate, or both not being sinusoidal signals.

Range-vitals transform engine 213 may perform a transform similar to a range-doppler transform with several possible differences. Since phase shifts are used rather than velocity, the data input to the transform has different properties. The FMCW operates in a continuous space-sampling mode over long periods of time (rather than a burst fast-sampling mode over a short period of time). Additionally, as previously detailed, zero padding is performed to allow for sufficient resolution for accurate determination of heartrate and breathing rate.

Range gating filter 214 is used to monitor only a defined range of interest and exclude waveform data due to movement beyond the defined range of interest. For arrangements detailed herein, the defined range of interest may be 0 to 1 meter. In some embodiments, this defined range of interest may be different or possibly set by a user or service provider. A goal of this arrangement may be to monitor only the one person closest to the device (and exclude any other person farther away, such as a person sleeping next to the person being monitored). Range and range gating filter 214 serves to remove movement data attributed to objects outside of the defined range of interest and sum the energy of movement data attributed to objects within the defined range of interest.

Spectral summation engine 215 may receive the output from range gating filter 214. Spectral summation engine 215 may function to transfer the measured energy of harmonic frequencies of the heartrate and breathing rate and sum the harmonic frequency energy onto the fundamental frequency's energy. This function can be referred to as a harmonic sum spectrum (HSS). Heartrate and breathing rate are not sinusoidal, therefore, in the frequency domain, harmonics will be present at frequencies higher than the fundamental frequency of the user's breathing rate and the fundamental frequency of the user's heartrate. One of the primary purposes of spectral summation engine 215 is to prevent harmonics of the monitored user's breathing rate from affecting the frequency measurement of the monitored user's heartrate (or the reverse). The HSS may be performed at the second order by summing the original spectrum with a down-sampled instance (by a factor of two) of the spectrum. This process may be repeated such that higher order harmonics are added to the fundamental frequency.

At this stage, for a person in bed who is lying still (with the exception of movement due to breathing and heartrate), it will be expected that two major frequency peaks will present in the frequency data. However, if the monitored user is physically moving, such as rolling over in bed, the energy will be significant distributed across the frequency spectrum (a broadband distribution). Such large physical movement may manifest itself in the frequency data as being a large number of small peaks. If the bed is empty, rather than a person being present, there may be no or almost no frequency components above the noise floor since movement filter 211 has previously filtered raw waveform data corresponding to static objects.

Spectral summation engine 215 may output an indication of heartrate (e.g., in beats per minute) and breathing rate (e.g., in breaths per minute). Neural network 216 may be used to determine whether the heartrate and/or breathing rate output by spectral summation engine 215 should be considered valid. Neural network 216 may be trained (e.g., using supervised learning performed using a training set of data) to distinguish at least three states, such as those indicated in Table 2 by performing a spectral analysis. Each state in Table 2 is associated with a different spectral energy and sparsity profile. The neural network may be trained to distinguish between each state based on the spectral energy profile output by spectral summation engine 215.

TABLE 2

| State of Monitored Region | Spectral Energy | Spectral Sparsity |
|---|---|---|
| User present and vitals-only movement | High | Low |
| User present and moving (limb and torso movements) | High | High |
| No user present | Low | Low |

The state of the monitored region determined by neural network 216 may be used in determining the monitored user's sleep state. The state of the monitored region determined by neural network 216 may further be used to determine if the vital statistics output by spectral summation engine 215 should be trusted or ignored. For accurate vital statistic determination, heartrate and breathing rate may only be identified as likely accurate when neural network 216 determines that the user is present and still (i.e., no large physical movements, however movement is occurring due to breathing and/or heartbeat). The vital statistics output by spectral summation engine 215 may only be stored locally or may be transmitted to cloud server system 250 for remote storage.

Neural network 216 may be initially trained using a large set of training data that has been properly classified as mapping the spectral frequency profile of the specific output of spectral summation engine 215 to the ground-truth user state. The neural network may be a fully connected neural network that is not time-dependent. In some embodiments, a machine-learning arrangement, classifier, or other form of artificial intelligence other than a neural network may be used.

The sleep state determined by neural network 216 may be stored, along with time data, to sleep data datastore 220. The vital statistics output by spectral summation engine 215 may only be stored to vital statistic datastore 230 when neural network 216 indicates that the monitored user is present and still. Other vital statistic data may be discarded or possibly flagged to indicate it is less likely to be correct. The data stored to sleep data datastore 220 and vital statistic datastore 230 may be stored only locally at smart home device 201. Such an implementation may help alleviate a concern about health-related data being transmitted and stored remotely. In some embodiments, the monitored user may elect to have sleep data and vital statistic data transmitted via network interface 203, stored, and analyzed externally, such as by cloud server system 250. Storage by cloud server system 250 may have significant benefits, such as the ability for the user to access such data remotely, allow access to a medical provider, or participate in research studies. The user may retain the ability to delete or otherwise remove the data from cloud server system 250 at any time.

In some embodiments, processing module 210 may be wholly or partly located remotely from smart home device 201. While radar subsystem 205 may need to be local to the monitored user, the processing of processing module 210 may be moved to cloud server system 250. In other embodiments, another smart home device that is in local communication (e.g., via a LAN or WLAN) with smart home device 201 may perform some or all of the processing of processing module 210. In some embodiments, a local communication protocol, such as involving a mesh network, can be used to transmit the raw waveform data to the local device that will be performing the processing. Such communication protocols can include Wi-Fi, Bluetooth, Thread, or communication protocols of the IEEE 802.11 and 802.15.4 families.

Similar to the processing, storage of the sleep data and vital statistic data may occur at cloud server system 250 or another smart home device location to smart home device 201. In still other embodiments, processing module 210 may be incorporated with radar subsystem 205 as a single component or system of components.

The stored sleep data of sleep data datastore 220 and the vital statistic data of vital statistic datastore 230 may be used to provide the user with short-term and long-term visual and trends relating to his sleeping patterns, vital statistics, or both. For instance, each morning, representation engine 217 may output or make available graphs, statistics, and trends. For example, a graph that is indicative of sleep data from the previous night and, possibly one or more graphs indicative of breathing rates and heartrate during the previous night. Similar graphs, trends, and statistics may be output for significantly longer periods of time, such as weeks, months, years, and even multi-year stretches of time. Other uses for sleep data and vital statistics may be possible. For instance, if certain triggers regarding heartrate, breathing rate, and/or sleeping patterns are triggered a medical professional may be notified. Additionally or alternatively, a notification may be output to the user indicating that the collected data is potentially concerning or is indicative of a healthy person. In some instances, specific sleep problems may be identified, such as sleep apnea.

Figure 3:
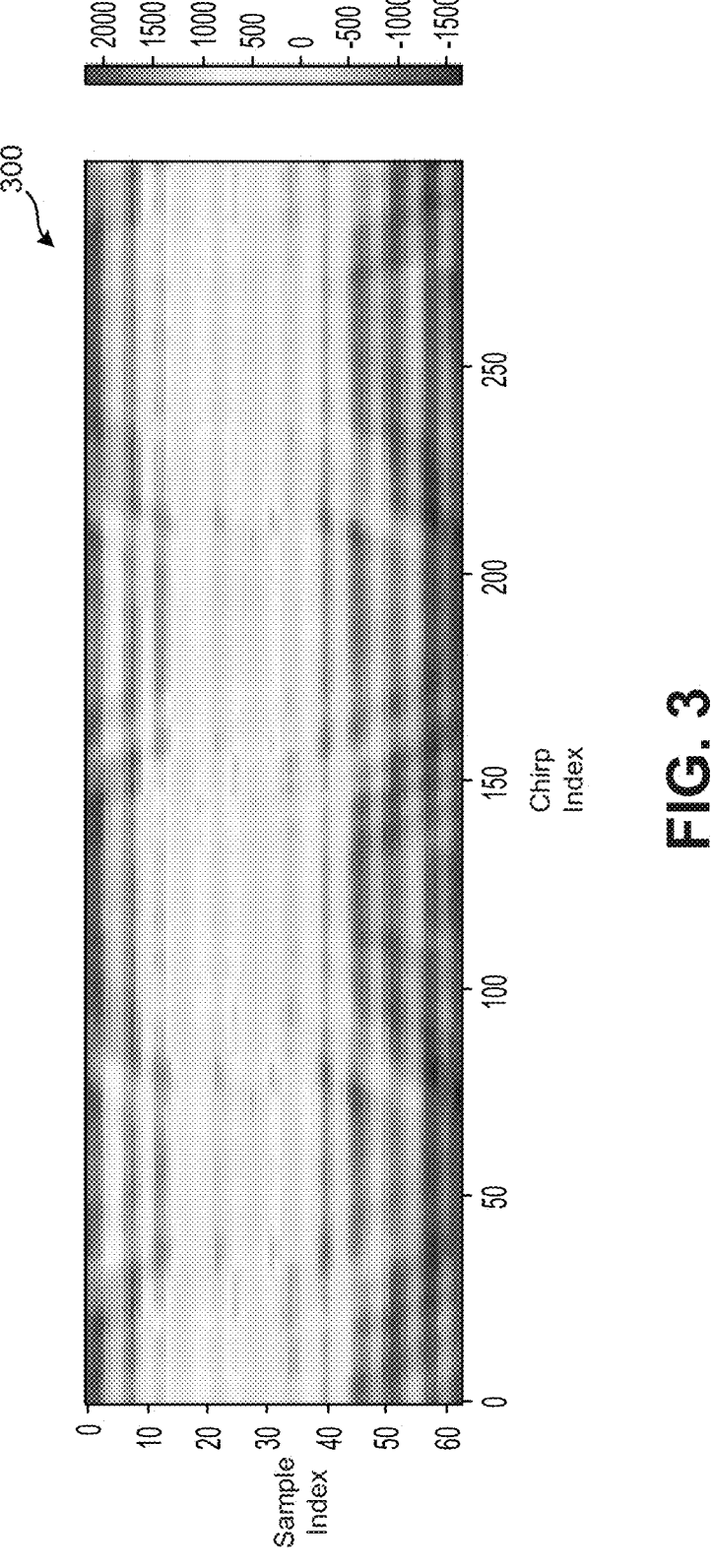
FIG. 3 illustrates an embodiment of waveform data in which movement due to vital signs of a user are observable.

FIG. 3 illustrates an embodiment 300 of raw waveform data in which movement due to vital signs of a user are observable. Embodiment 300 is representative of smart home device 201 being aimed at a monitored sleeping user from a distance of less than one meter who is generally still. In embodiment 300, slight "waves" are visible in the raw waveform data. These waves are caused by the user's breathing pattern at approximately 13.5 breaths per minute. Along the x-axis, each chirp index corresponds to a received chirp of radio waves prior to any processing by movement filter 211. Therefore, for each chirp-index along the x-axis, sixty-four samples were taken as indicated by the sample index on the y-axis. For each of these samples, a value is measured to indicate RF intensity. In embodiment 300, a large portion of the raw waveform data is due to static objects. Due to such a large portion of the data being indicative of radio waves reflected by static objects, this raw waveform data is first filtered out by movement filter 211.

Figure 4:
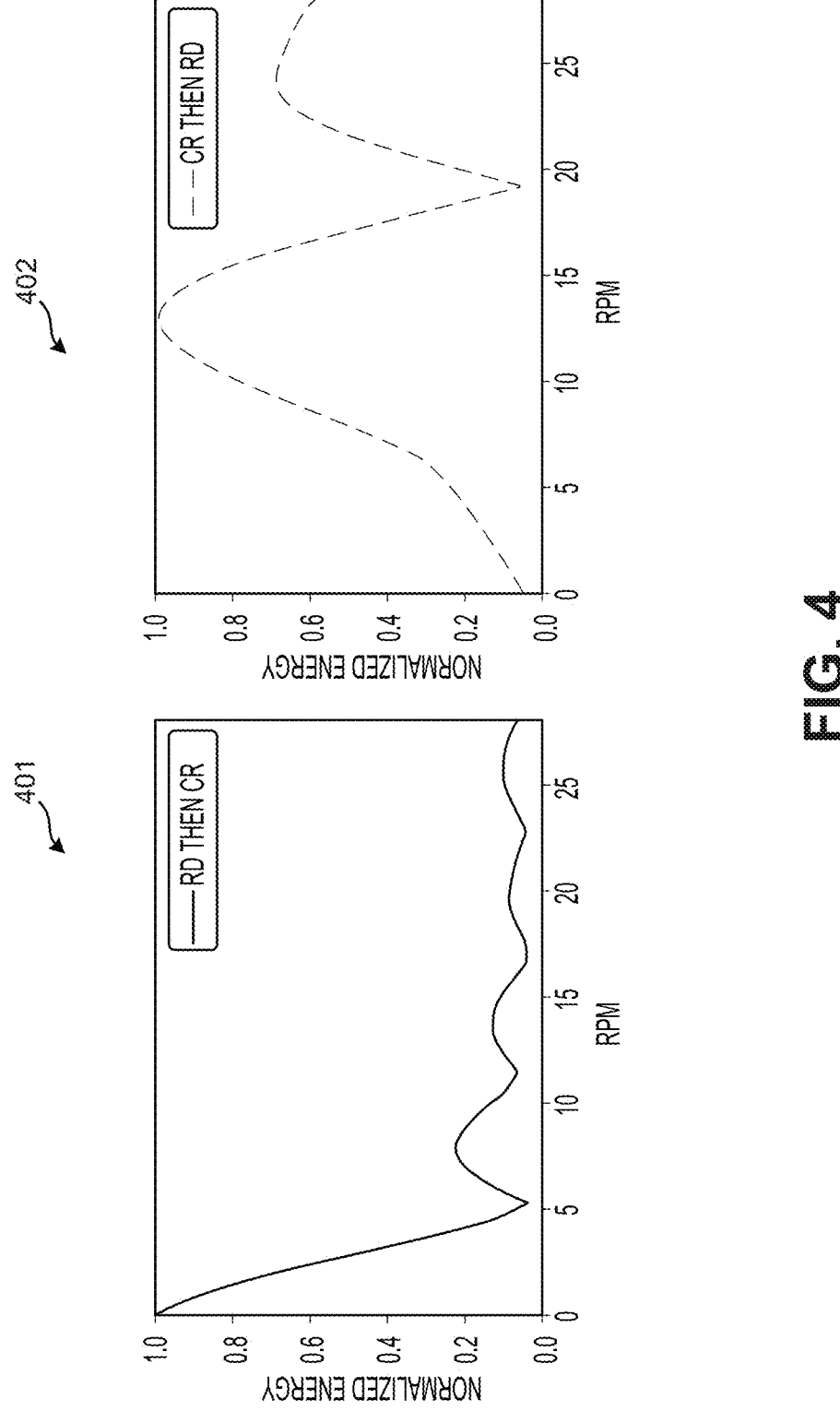
FIG. 4 illustrates an embodiment of two frequency-domain graphs indicative of energy level at different frequencies.

FIG. 4 illustrates an embodiment 400 of two frequency-domain graphs indicative of energy level. In graph 401, without any motion-based filtering having been performed before analyzing the raw waveform data, it can be seen that by far the most energy is present at and around a frequency of zero. This high level of energy at low frequencies may be caused by static objects in combination with zero padding. However, in graph 402, motion-based filtering has been performed by movement filter 211, such that energy related to static objects has been removed. This removal allow for a clear peak to be seen around 13.5 respirations per minute (rpm). It should be understood that if movement due to the user's heartbeat is being measured, the x-axis of graph 402 could be extended (and reflect frequency, rather than rpm) such that a second significant peak at the user's heartrate would be visible.

Figure 5:
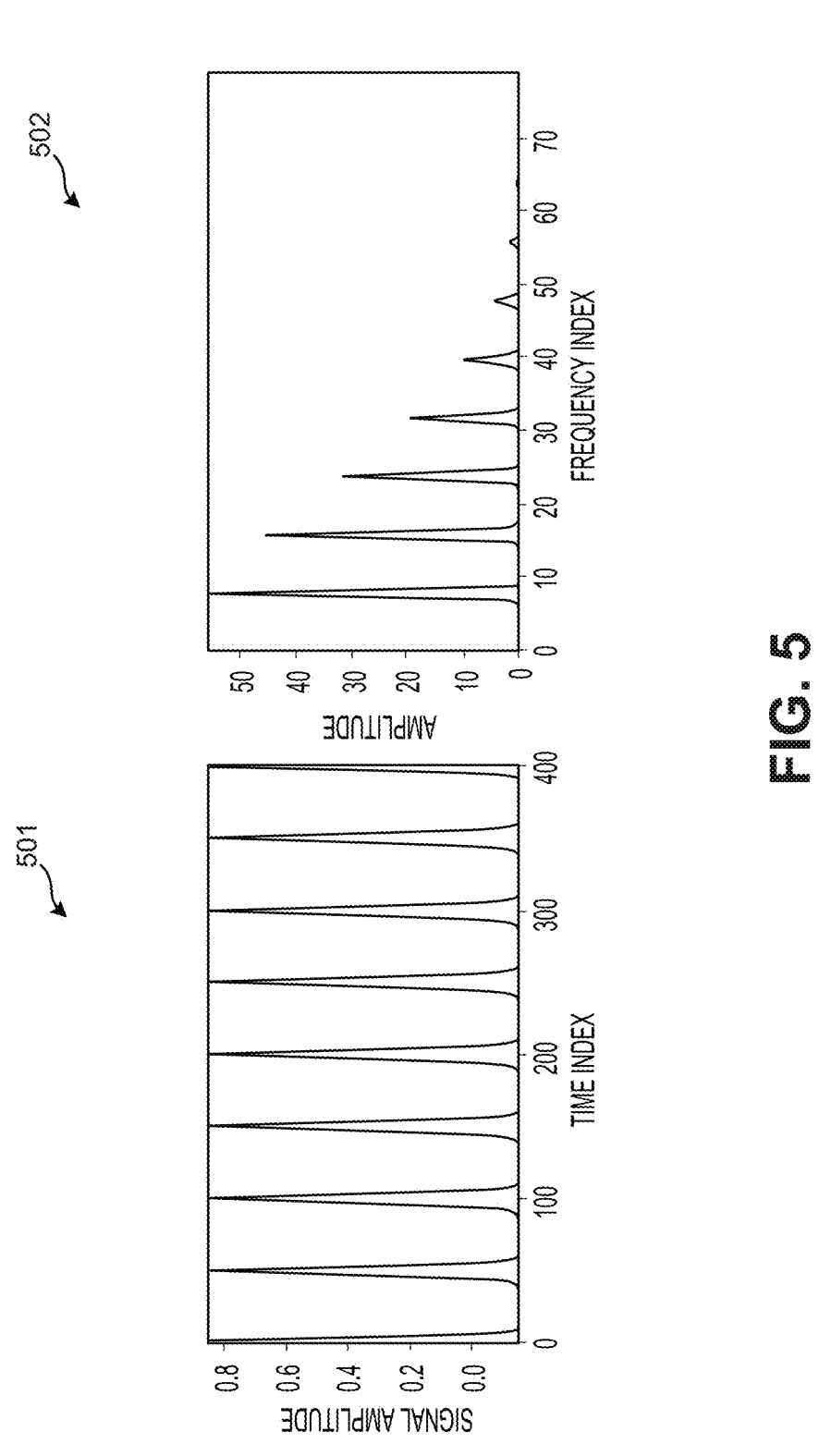
FIG. 5 illustrates an embodiment of two graphs indicative of the impulse nature of a human vital sign, such as heartrate.

FIG. 5 illustrates an embodiment 500 of two graphs indicative of the impulse nature of a vital sign, such heartrate. A heart may typically be beating for ⅛ of the time it is resting. In graph 501, periodic impulses are illustrated over time, which can be indicative of chest displacement due to breathing or chest displacement due to a heartbeat. When converted to the frequency domain in graph 502, a fundamental frequency and many higher harmonic frequencies are present due to the measured data of graph 501 not being a sinusoid. These upper harmonic values may be identified and summed with the fundamental frequency by spectral summation engine 215.

Figure 6:
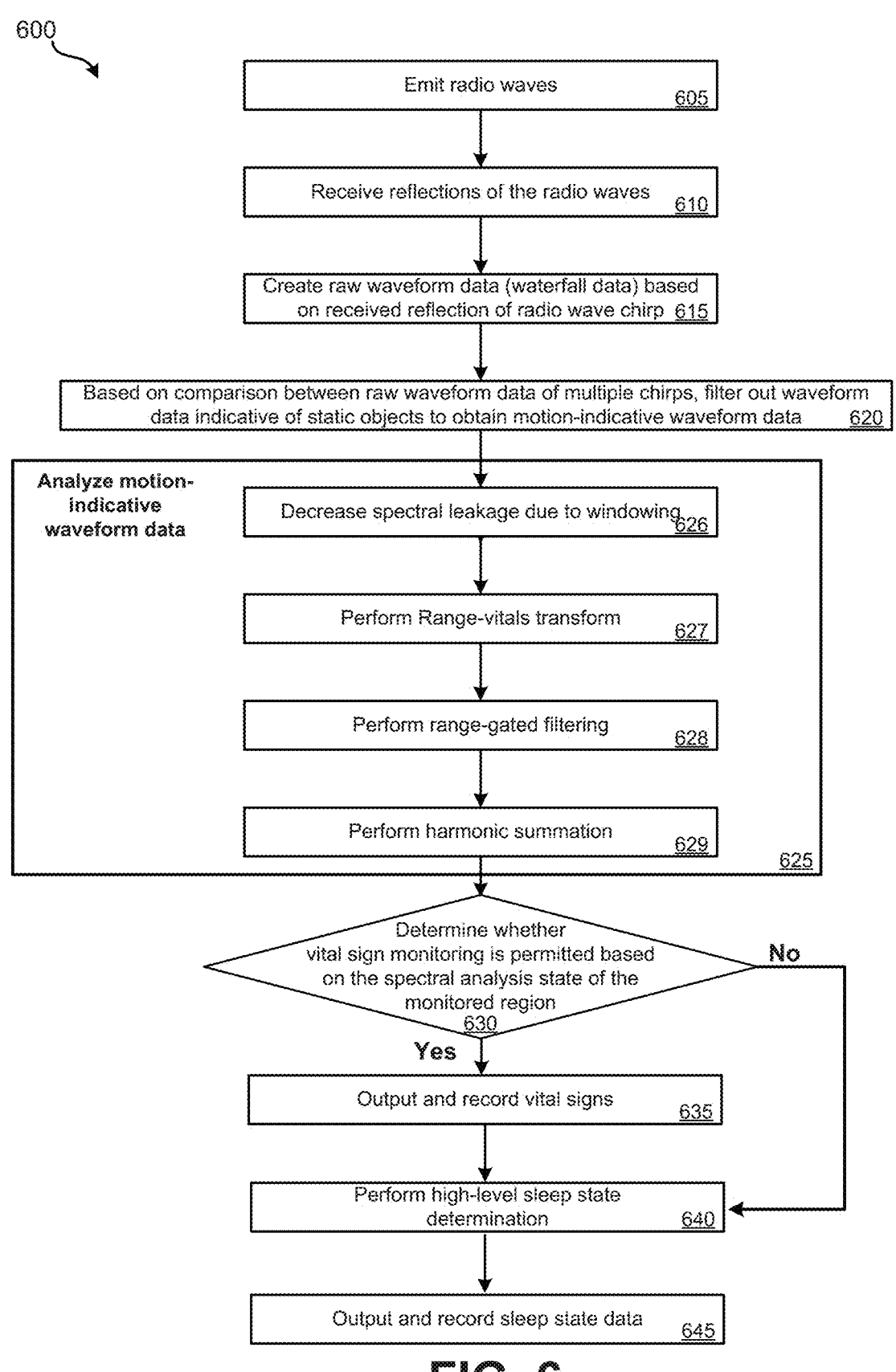
FIG. 6 illustrates an embodiment of a method for using low power radio waves to perform sleep tracking and vital sign monitoring.

Various methods may be performed using system 200. FIG. 6 illustrates an embodiment of a method 600 for using low power radio waves to perform sleep tracking and vital sign monitoring. Method 600 may be performed using system 200 or some other form of system that can transmit, receive, and analyze radar, such as an FMCW radar. At block 605, radio waves may be emitted. The radio waves emitted may be continuous-wave radar, such as FMCW. The FMCW radar may operate in a continuous sparse-sampling mode over a relatively long period of time. The radio waves emitted may be emitted by RF emitter 206 of radar subsystem 205. At block 610, reflections of the radio waves may be received, such as by RF receiver 207 of radar subsystem 205. The reflections received at block 610 may be reflected off of moving objects (e.g., a person having a heartbeat and breathing) and stationary objects. A phase shift may be present in the radio waves reflected by a moving object.

At block 615, raw waveform data, which can also be referred to as waterfall data, may be created based on received reflected radio waves. The reflected radio waves may be indicative of distance and a phase shift. At a given frequency, such as 10 Hz, a number of samples may be taken, such as 64 samples. For each of these samples, intensity and phase shift may be measured. Over time, a window of raw waveform data may be created and stored in a buffer for analysis. Referring to FIG. 2, block 615 may be performed by radar processing circuit 208 or by processing module 210.

At block 620, samples of the waveform data that have been buffered may be compared. Waveform data that is indicative of static objects (that is, zero phase shift), which can be defined as objects having movement below a particular frequency (or at least a threshold phase shift), may be filtered out and discarded such that only waterfall data that is indicative of movement above a particular frequency is saved for further analysis. The particular frequency may be defined based on characteristics of the person to be monitored, such as age, as detailed in Table 1. Block 620 may be performed before block 625 to remove a large portion of the waveform data attributed to static objects and more readily make data attributed to small movements of a user attributed to vital signs be detectable.

At block 625, the motion-indicative waveform data may be analyzed. This analysis may be performed to identify and separate data attributable to heartrate and breathing rate. Block 625 may be broken down into multiple blocks; in some embodiments, only a subset of these blocks may be performed and/or the order of such blocks may be varied.

At block 626, a window of raw waveform data is to be analyzed through block 625, the Fourier transform of the windowed raw waveform data develops non-zero values at frequencies other than the fundamental frequency due to spectral leakage. To deemphasize artifacts in the frequency domain due to spectral leakage, a particular type of window may be applied, such as a Hamming window. Such a window may help emphasize the fundamental frequencies due to vital signs within the window but deemphasize artifacts due to spectral leakage. While a Hamming window has been found to be effective, other forms of windowing may be used, such as a Hann window, a Parzen window, or a triangular window.

At block 627, a range-vitals transform may be performed. As part of the range-vitals transform, zero-padding may be performed. This zero-padding may help increase the frequency resolution to accurately identify the frequency of vital signs, such as breathing and heartrate. Further, as part of range-vitals transform, a Fourier transform may be performed to convert waveform data into the frequency domain.

At block 628, range-gated filtering may be performed. Block 628 may be performed by Block 628 may be performed by range gating filter 214 of processing module 210 or some other processing system. to exclude spectral energy from the waveform data attributed to objects outside of a defined distance range. Block 628 may be performed in order to ensure that only a user closest to the radar emitter/receiver (e.g., radar subsystem 205) is monitored to the exclusion of other persons or animals in the vicinity (e.g., sleeping next to the user being monitored).

At block 629, a harmonic summation may be performed. Block 629 may be performed by spectral summation engine 215 of processing module 210 or by some other processing system. The harmonic summation may function to transfer the measured energy of harmonic frequencies of the heartrate and breathing rate and sum the harmonic frequency energy onto the fundamental frequency's energy. Heartrate and breathing rate are not sinusoidal, therefore, in the frequency domain, harmonics will be present at frequencies higher than the fundamental frequency of the user's breathing rate and the fundamental frequency of the user's heartrate.

At block 630, a determination may be made whether the vital sign monitoring is currently permitted. Vital sign monitoring may only be judged to be accurate when the monitored user is in bed and is not moving (other than the small movements due to vital signs). A state analysis may be performed as detailed in relation to FIG. 7 to determine if the monitored user is in bed, not moving, and in a position to have vital signs monitored. Block 630 may be performed using a trained neural network that can distinguish between various user states. Only when a user is lying still in bed may block 630 proceed to block 635. Otherwise, block 630 may proceed to block 640.

At block 635, vital sign data calculated via block 625 may be stored and/or combined with other vita sign data. Vital sign data may only be stored locally to help protect the monitored user's privacy. Alternatively, the vital sign data may be securely transmitted and stored at a cloud-based server which the monitored user has previously authorized for use in storage of his vital sign data. Before vital sign data is transmitted off of the device performing the monitoring, the user can be required to provide explicit permission that such transmission is to occur, where the vital sign data will be stored, how long the vital sign data will be stored, and how such vital sign data will be used. In some embodiments, the vital sign data is output for presentation and is not stored for longer than is necessary for presentation.

At block 640, a high-level sleep inference may be performed. The high-level sleep inference may determine, whether or not the user is present in bed, whether the user is entering or exiting bed, when the user is performing large movements (e.g., rolling over, tossing and turning, etc.), or if the user is getting high-quality sleep (e.g., laying still). Similar to vital sign data of block 635, such data may be output and/or recorded. Sleep state data may only be stored locally to help protect the monitored user's privacy. Alternatively, the sleep state data may be securely transmitted and stored at a cloud-based server that the monitored user has previously authorized for use in storage of his sleep state data. Before sleep state data is transmitted off of the device performing the monitoring, the user can be required to provide explicit permission that such transmission is to occur, where the sleep state data will be stored, how long the sleep state data will be stored, and how such sleep state data will be used. In some embodiments, the sleep state data is output for presentation and is not stored for longer than is necessary for presentation.

Figure 7:
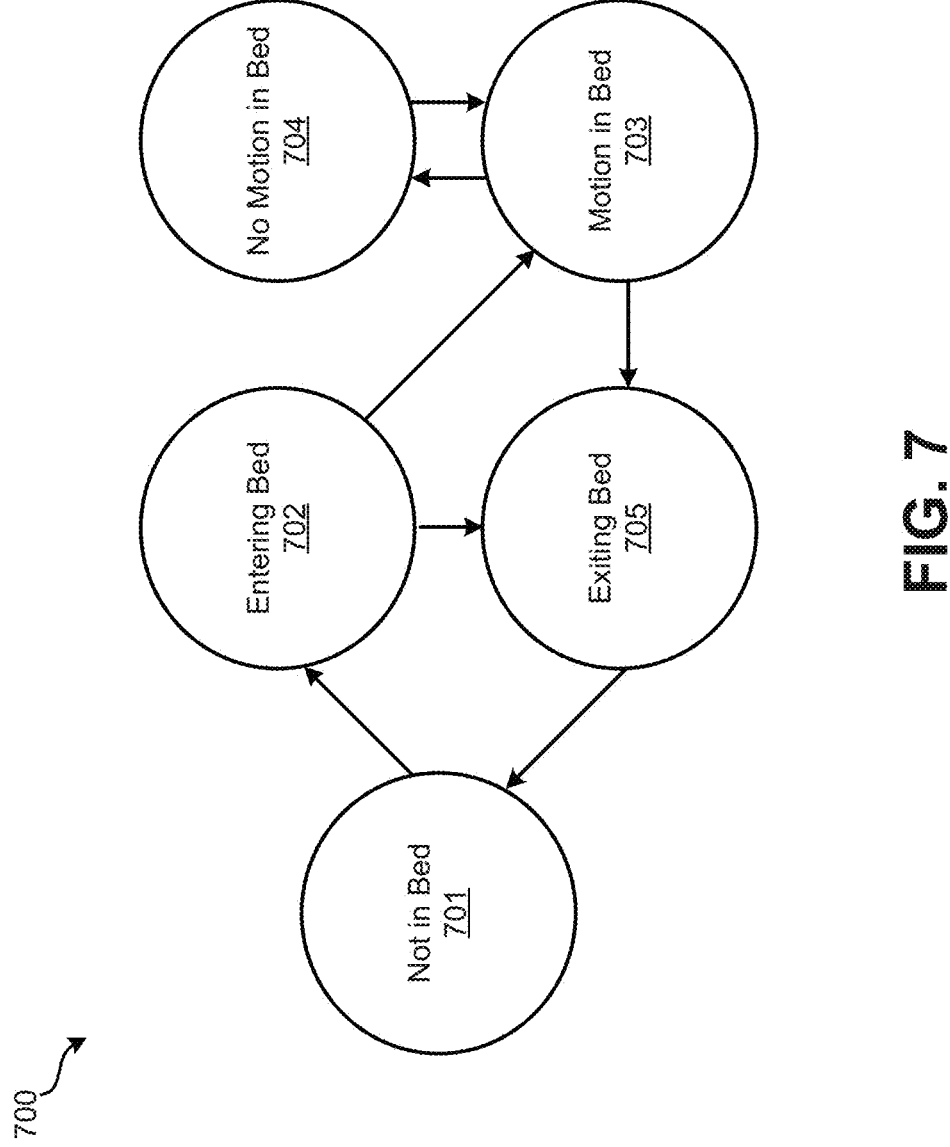
FIG. 7 illustrates an embodiment of a state diagram for determining when tracking of vital signs is permitted.

FIG. 7 illustrates an embodiment 700 of a state machine for tracking a monitored user's sleep state. Embodiment 700 may be used as part of block 640 for determining a user's current sleep state. Embodiment 700 may include five possible sleep states: entering bed state 701; not in bed state 702; motion in bed state 703; no motion in bed state 705; and exiting bed state 704.

If no motion-indicative waveform data is present, this may be indicative that the user is not in bed. A user who is in bed can be expected to always be moving in at least small amounts due to their vital signs. Therefore, if zero movement is observed, the user may be judged to be in state 701. Following state 701 being determined, the next possible state that may be determined is state 702. In state 702, in state 702, the monitored user is entering bed. Significant user motion may be sensed, such as according to Table 2. This may be indicative of a user entering bed and may cause the state to transition from state 701 to state 702.

From state 702, motion may continue to be detected in bed, such as due to the user rolling around, getting positioned, moving pillows, sheets, and/or blankets, reading a book, etc. state 702 may transition to state 703 while such motion continues to be detected. Alternatively, if motion is detected then zero motion is detected, this may be indicative that state 705 has been entered by the monitored user exiting bed. If this condition occurs, state 702 may transition to state 705, then back to state 701.

From state 703, the monitored user may be determined to be exiting bed at state 705 may be become motionless at state 704. To be "motionless" at state 704 refers to no large movements being performed by the monitored user, but he user continuing to perform small motions due to vital signs. In some embodiments, only when the monitored user's state is determined to be state 704 are vital signs treated as accurate and/or stored, recorded, or otherwise used to measure the user's vital signs. Data collected during state 703 and state 704 may be used to determine the monitored user's general sleep patterns (e.g., how much time tossing and turning, how much quality sleep, when deep sleep occurred, when REM sleep occurred, etc.).

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered.

What is claimed is:

1. A system that performs radar-based measurement of vital signs, the system comprising:
   a processing system, comprising one or more processors, that is in communication with a radar subsystem, the processing system being configured to:
   analyze radar waveform data;
   perform, using a trained machine learning arrangement, a classification based on multiple spectral characteristics of the analyzed radar waveform data to determine a state of a monitored region, wherein:
   the trained machine learning arrangement is trained using a set of training data in which the set of training data is classified as mapping multiple spectral characteristics to ground-truth user states; and
   the trained machine learning arrangement classifies the analyzed radar waveform data into a plurality of states, comprising a first state in which a user is present in the monitored region and the user is performing vitals-only movement and a second state which is different from the first state;
   initiate, based on the state of the monitored region being in the first state, vital sign monitoring of the user;
   determine, using the trained machine learning arrangement based on analyzing the radar waveform data, one or more vital signs of the user present within the monitored region; and
   record the one or more determined vital signs of the user.

2. The system of claim 1, wherein the system further comprises:
   a housing;
   an RF emitter located within the housing; and an RF receiver located within the housing, wherein the housing is configured to be positioned such that a field of view of the RF receiver is pointed toward the monitored region that includes the user in bed.

3. The system of claim 2, further comprising a radar processing circuit located within the housing that processes data received from the RF receiver and outputs raw waveform data.

4. The system of claim 3, wherein the processing system is located within the housing.

5. The system of claim 3, wherein the processing system is further configured to:

receive the raw waveform data from the radar processing circuit, wherein the processing system being configured to analyze the radar waveform data comprises the processing system being configured to:

filter, from the raw waveform data, waveform data indicative of static objects to obtain motion-indicative waveform data.

6. The system of claim 5, wherein the processing system is further configured to:

filter one or more frequencies of the filtered waveform data to sum harmonics of the one or more frequencies caused by the one or more vital signs.

7. The system of claim 2, wherein the RF emitter emits frequency-modulated continuous-wave (FMCW) radar.

8. The system of claim 1, wherein the second state indicates the user is present and moving.

9. The system of claim 1, wherein the second state indicates the user is not present.

10. The system of claim 1, wherein the processing system being configured to perform, using the trained machine learning arrangement, the classification comprises the processing system being further configured to use a neural network to perform the classification based on spectral energy and spectral sparsity.

11. The system of claim 1, further comprising:

a smartphone housing the processing system; and a smartphone charger stand, wherein the smartphone is docked with the smartphone charger stand such that a radar sensor of the smartphone is pointed to emit radio waves at a location where the user will be sleeping.

12. The system of claim 1, wherein the one or more vital signs comprises a breathing rate, a heartrate, or both.

13. A method for radar-based measurement of vital signs, the method comprising:

analyzing by a processing system comprising one or more processors, radar waveform data;

performing, by the processing system, using a trained machine learning arrangement, a classification based on multiple spectral characteristics of the analyzed radar waveform data to determine a state of a monitored region, wherein:

the trained machine learning arrangement is trained using a set of training data in which the set of training data is classified as mapping multiple spectral characteristics to ground-truth user states; and the trained machine learning arrangement classifies the analyzed radar waveform data into a plurality of states, comprising a first state in which a user is present and is performing vitals-only movement and a second state which is different from the first state;

permitting, by the processing system based on the monitored region being in the first state, vital sign monitoring;

determining, by the processing system using the trained machine learning arrangement based on analyzing the radar waveform data, one or more vital signs of the user present within the monitored region; and recording, by the processing system to a non-transitory processor-readable medium, an indication of the one or more determined vital signs of the user.

14. The method of claim 13, wherein performing the classification comprises using, by the processing system, a neural network to perform the classification based on spectral energy and spectral sparsity.

15. The method of claim 13, further comprising:

emitting, by an RF emitter located within a same housing as the processing system, radio waves, wherein the emitted radio waves are emitted as part of frequency-modulated continuous-wave (FMCW) radar waves; and receiving, by an RF receiver located within the same housing as the processing system, reflections of the radio waves.

16. The method of claim 15, further comprising: processing, by a radar processing circuit distinct from the processing system, the reflections of the radio waves from the RF receiver and outputs raw waveform data.

17. The method of claim 16, further comprising: filtering, by the processing system, from the raw waveform data, waveform data indicative of static objects to obtain motion-indicative waveform data.

18. The method of claim 16, wherein the processing system, the radar processing circuit, the RF emitter, and the RF receiver are part of a smartphone, the method further comprising:

docking the smartphone with a charger stand such that the RF emitter of the smartphone is pointed to emit the radio waves at the monitored region where the user will be sleeping.

19. A non-transitory processor-readable medium comprising process-readable instructions configured to cause one or more processors to:

analyze radar waveform data;

perform, using a trained machine learning arrangement, a classification based on multiple spectral characteristics of the analyzed radar waveform data to determine a state of a monitored region, wherein:

the trained machine learning arrangement is trained using a set of training data in which the set of training data is classified as mapping multiple spectral characteristics to ground-truth user states; and the trained machine learning arrangement classifies the analyzed radar waveform data into a plurality of states, comprising a first state in which a user is present in the monitored region and is performing vitals-only movement and a second state which is different than the first state;

initiate, based on the state of the monitored region being in the first state, vital sign monitoring of the user;

determine, using the trained machine learning arrangement based on the analyzing the radar waveform data, one or more vital signs of the user present within the monitored region; and record the one or more determined vital signs of the user.

20. The non-transitory processor-readable medium of claim 19, wherein the one or more processors are configured to use a neural network to perform the classification based on spectral energy and spectral sparsity.

* * * * *